(12) United States Patent
Jamiolkowski et al.

(10) Patent No.: US 9,737,630 B2
(45) Date of Patent: Aug. 22, 2017

(54) MECHANICALLY STRONG ABSORBABLE POLYMERIC BLEND COMPOSITIONS OF PRECISELY CONTROLLABLE ABSORPTION RATES, PROCESSING METHODS, AND PRODUCTS THEREFROM

(71) Applicant: Ethicon, Inc., Somerville, NJ (US)

(72) Inventors: Dennis D. Jamiolkowski, Long Valley, NJ (US); Daniel Steiger, Basking Ridge, NJ (US); Modesto Erneta, Princeton Junction, NJ (US)

(73) Assignee: Ethicon, LLC, San Lorenzo, PR (US)

( * ) Notice: Subject to any disclaimer, the term of this patent is extended or adjusted under 35 U.S.C. 154(b) by 0 days.

(21) Appl. No.: 14/635,215

(22) Filed: Mar. 2, 2015

(65) Prior Publication Data

US 2015/0174288 A1    Jun. 25, 2015

Related U.S. Application Data

(62) Division of application No. 13/833,690, filed on Mar. 15, 2013.

(60) Provisional application No. 61/651,353, filed on May 24, 2012.

(51) Int. Cl.
| | | |
|---|---|---|
| *A61L 17/12* | (2006.01) | |
| *A61L 27/26* | (2006.01) | |
| *A61L 27/54* | (2006.01) | |
| *A61B 17/064* | (2006.01) | |
| *B29C 45/00* | (2006.01) | |
| *B29C 47/00* | (2006.01) | |
| *B29C 49/00* | (2006.01) | |
| *C08L 67/04* | (2006.01) | |
| *A61L 17/00* | (2006.01) | |
| *A61B 17/06* | (2006.01) | |
| *C08J 3/00* | (2006.01) | |
| *A61B 17/00* | (2006.01) | |
| *B29L 31/00* | (2006.01) | |

(52) U.S. Cl.
CPC ........ *A61L 17/12* (2013.01); *A61B 17/06166* (2013.01); *A61L 17/005* (2013.01); *A61L 27/26* (2013.01); *A61L 27/54* (2013.01); *B29C 45/00* (2013.01); *B29C 47/00* (2013.01); *B29C 49/00* (2013.01); *C08J 3/005* (2013.01); *C08L 67/04* (2013.01); *A61B 17/064* (2013.01); *A61B 2017/00004* (2013.01); *A61L 2300/202* (2013.01); *A61L 2300/404* (2013.01); *A61L 2300/606* (2013.01); *A61L 2430/00* (2013.01); *B29L 2031/753* (2013.01); *C08J 2367/04* (2013.01); *C08J 2467/04* (2013.01); *Y10T 442/10* (2015.04); *Y10T 442/3976* (2015.04); *Y10T 442/40* (2015.04); *Y10T 442/696* (2015.04)

(58) Field of Classification Search
None
See application file for complete search history.

(56) References Cited

U.S. PATENT DOCUMENTS

| | | | |
|---|---|---|---|
| 7,524,891 B2 | 4/2009 | Rose et al. | |
| 8,354,476 B2 * | 1/2013 | Hanes | A61K 47/48192 525/327.4 |
| 2005/0048099 A1 * | 3/2005 | Shiah | A61K 9/0051 424/428 |
| 2006/0045912 A1 * | 3/2006 | Truog | A61K 9/282 424/468 |
| 2007/0149640 A1 | 6/2007 | Andjelic et al. | |
| 2009/0118241 A1 | 5/2009 | Andjelic et al. | |
| 2009/0274742 A1 | 11/2009 | Brown | |
| 2011/0245172 A1 | 10/2011 | Norton et al. | |

FOREIGN PATENT DOCUMENTS

| | | |
|---|---|---|
| EP | 853949 | 4/2003 |
| WO | WO 97/26869 | 7/1997 |

\* cited by examiner

*Primary Examiner* — David J Blanchard
*Assistant Examiner* — Sarah Chickos
(74) *Attorney, Agent, or Firm* — E. Richard Skula

(57) ABSTRACT

Novel absorbable polymer blends are disclosed. The blends are useful for manufacturing medical devices having engineered degradation and breaking strength retention in vivo. The blends consist of a first absorbable polymeric component and a second absorbable polymeric component. The weight average molecular weight of the first polymeric component is higher than the weight average molecular weight of the second polymeric component. At least at least one of said components is at least partially end-capped by a carboxylic acid group. Further aspects are medical devices made therefrom.

15 Claims, 8 Drawing Sheets

MECHANICALLY STRONG ABSORBABLE POLYMERIC BLEND COMPOSITIONS OF PRECISELY CONTROLLABLE ABSORPTION RATES, PROCESSING METHODS, AND PRODUCTS THEREFROM

CROSS REFERENCE TO RELATED APPLICATION

This application is a divisional of co-pending application Ser. No. 13/833,690 filed on Mar. 15, 2013 which claims priority to U.S. Provisional application 61/651,353 filed May 24, 2012.

FIELD OF THE INVENTION

The field of art to which this invention relates is absorbable polymers, in particular, absorbable polymer blends useful for manufacturing medical devices, especially sutures, possessing high initial mechanical strength and controlled loss of mechanical properties post-implantation and/or controlled absorption time.

BACKGROUND OF THE INVENTION

Absorbable polymers and medical devices made from such polymers are known in the art. Conventional absorbable polymers include polylactic acid, poly(p-dioxanone), polyglycolic acid, co-polymers of lactide, glycolide, p-dioxanone, trimethylene carbonate, $\epsilon$-caprolactone, in various combinations, etc. The chemistry of absorbable polymers is designed such that the polymers breakdown in vivo, for example by hydrolysis, and the byproducts metabolized or otherwise excreted from the patient's body. The advantages of utilizing implantable medical devices made from absorbable polymers are numerous and include, for example, eliminating the need for additional surgeries to remove an implant after it serves its function. In the case of a wound closure function, when a "temporary presence" of the implant is desired, ideally support can be provided until the tissue heals.

Absorbable is meant to be a generic term, which may also include bioabsorbable resorbable, bioresorbable, degradable or biodegradable.

The absorbable polymers conventionally used to manufacture medical devices have been on occasion polymeric blends of absorbable polymers and co-polymers engineered to provide specific characteristics and properties to the manufactured medical device, including absorption rates, mechanical property (e.g., breaking strength) retention post-implantation, and dimensional stability, etc.

There are many conventional processes used to manufacture medical devices from absorbable polymers and polymer blends. The processes include injection molding, solvent casting, extrusion, machining, cutting and various combinations and equivalents. A particularly useful and common manufacturing method is thermal forming using conventional injection molding processes and extrusion processes.

The retention of mechanical properties post-implantation is often a very important feature of an absorbable medical device. The device must retain mechanical integrity until the tissue has healed sufficiently. In some bodily tissues, healing occurs more slowly, requiring an extended retention of mechanical integrity. This is often associated with tissue that has poor vascularization. Likewise there are other situations in which a given patient may be prone to poor healing: e.g., the diabetic patient. There are however many situations in which rapid healing occurs, which require the use of fast absorbing medical devices such as sutures; this is often associated with excellent vascularization. Examples of where such fast absorbing sutures can be used include certain pediatric surgeries, oral surgery, repair of the peritoneum after an episiotomy and superficial wound closures.

When rapid healing occurs, the mechanical retention profile of the medical device could reflect a more rapid loss in properties. Concomitant with this is the rate of absorption (bioabsorption or resorption), that is, the time required for the medical device to disappear from the surgical site.

One method that has been exploited to achieve the rapid loss of mechanical properties is the use of pre-hydrolysis and/or gamma irradiation. For instance Hinsch et al., in EP 0 853 949 B1, describe a process for reducing the resorption period of hydrolyzable resorbable surgical suture material, wherein the surgical suture material is incubated in a hydrolysis buffer, having an index of pH in the range from 4 to 10, for a period in the range from 10 hours to 100 hours at a temperature in the range from 30° C. to 65° C.

In order to shorten the absorption period of absorbable suture material it is also known to irradiate the suture material during the manufacture, e.g., by means of Co-60 gamma irradiation. Such an irradiation process produces defects in the polymer structure of the suture material, resulting in an accelerated decrease of the tensile strength and a shortened absorption period in vivo after implantation of the suture material. To use gamma irradiation in a manufacturing environment in order to reliably adjust in vivo absorption times and control post-implantation mechanical property loss is often difficult due to a variety of reasons. These reasons include the high precision required, and, the unintended damage to other important properties such as discoloration.

It is well known, however, that such treatments of pre-hydrolysis and gamma irradiation may have a negative effect on the mechanical properties of the device. Consequently, and for example, sutures that are touted as fast absorbing are often lower in initial strength than their standard absorbing suture counterparts.

In certain surgical procedures, the mechanical properties, particularly the tensile strength, of the wound closure device are clinically very important; in these wound closure devices, such as sutures, high strength is generally preferred. Commercially available braided fast absorbing suture sold by ETHICON, Inc., Somerville, N.J. 08876, and known as VICRYL RAPIDE™ (polyglactin 910) Suture exhibits a tensile strength of about 60 percent of the standard absorbing counterpart, Coated VICRYL™ (polyglactin 910) Suture.

There is a continuing need in this art for novel medical devices that lose their mechanical properties quickly and are absorbed rapidly, but which still provide high initial mechanical properties approaching those exhibited by their standard absorbing counterparts.

There have been attempts in the prior art to address the problem of rapid absorption. Rose and Hardwick in U.S. Pat. No. 7,524,891 describe the addition of certain carboxylic acids and their derivatives and anhydrides to poly(lactic acid) to make homogeneous blends, which exhibit a more rapid absorption. It should be noted that that they limit the amount of the additive to 10 weight percent. They clearly describe a system in which the additive is admixed throughout and is not reactive with the poly(lactic acid) so as to create a derivative.

There have been attempts in the prior art to address the problem of improved strength. For instance, Brown in US Patent Application Publication No. 2009/0274742 A1, entitled "Multimodal High Strength Devices And Composites", (hereinafter referred to as "'742") discloses an oriented implantable biodegradable multimodal device comprising a blend of a first polymer component having a first molecular weight together with at least a second polymer component having a molecular weight which is less than that of the first component, wherein polymer components within the blend are in uniaxial, biaxial or triaxial orientation. Brown speaks of achieving higher mechanical properties in blends of high molecular weight polylactide (e.g., IV=4.51 dL/g) with much lower molecular weight versions of this polymer (Mw=5,040 Da, Mn=3,827 Da), but only shows an increase in modulus and no increase in maximum stress. Additionally, Brown in '742 mentions a faster rate of absorption as compared to the high molecular weight polylactide when an additive is admixed in an amount of not more than 10% by weight of the polymer components.

A bimodal bioabsorbable polymer composition is disclosed in US Patent Application Publication US 2007/0149640 A1. The composition includes a first amount of a bioabsorbable polymer polymerized so as to have a first molecular weight distribution and a second amount of said bioabsorbable polymer polymerized so as to have a second molecular weight distribution having a weight average molecular weight between about 20,000 to about 50,000 Daltons. The weight average molecular weight ratio of said first molecular weight distribution to said second molecular weight distribution is at least about two to one, wherein a substantially homogeneous blend of said first and second amounts of said bioabsorbable polymer is formed in a ratio of between about 50/50 to about 95/5 weight/weight percent. Also disclosed are a medical device and a method of making a medical device.

In US 2009/0118241 A1, a bimodal bioabsorbable polymer composition is disclosed. The composition includes a first amount of a bioabsorbable polymer polymerized so as to have a first molecular weight distribution and a second amount of said bioabsorbable polymer polymerized so as to have a second molecular weight distribution having a weight average molecular weight between about 10,000 to about 50,000 Daltons. The weight average molecular weight ratio of said first molecular weight distribution to said second molecular weight distribution is at least about two to one, wherein a substantially homogeneous blend of said first and second amounts of said bioabsorbable polymer is formed in a ratio of between about 50/50 to about 95/5 weight/weight percent. Also disclosed are a medical device, a method of making a medical device and a method of melt blowing a semi-crystalline polymer blend.

Even though such polymer blends are known, there is a continuing need in this art for novel absorbable polymeric materials having precisely controllable absorption rates, that provide a medical device with improved characteristics including stiffness, retained strength in vivo (in situ), dimensional stability, absorbability in vivo, and manufacturability; there is a particular need for accelerated absorption and accelerated mechanical property loss post-implantation while still exhibiting high initial mechanical properties.

SUMMARY OF THE INVENTION

It is an object of the present invention to provide novel absorbable polymer blends that can be used in manufacturing processes to produce novel absorbable medical devices and medical device components by melt processes, such as extrusion or injection molding. When the medical device is in the form of a suture, said suture has superior mechanical properties (e.g., high breaking strength) at the time of implantation, as well as during the critical wound healing period, which is for example about 5 to 7 days post-implantation, when compared to a conventional suture with comparable composition. Once said critical wound healing period is over, said suture exhibits a rapid but controlled loss of mechanical properties within, for example approximately 14 days post-implantation, and a rapid but controlled absorption within, for example, approximately 42 days post-implantation.

Accordingly, a novel absorbable polymer blend composition is disclosed. The polymer blend is a mixture of a first absorbable polymeric component and a second absorbable polymeric component, wherein the first polymeric component has a weight average molecular weight higher than the weight average molecular weight of the second polymeric component, and wherein at least one of said components is at least partially end-capped by a carboxylic acid group.

The second polymeric component having lower weight average molecular weight can be also characterized as an oligomer or an oligomeric component.

In one aspect of the present invention, the absorbable polymer blend comprises a first absorbable polymeric component comprising about 65 weight percent to about 97.5 weight percent of a glycolide polymer or a lactide/glycolide copolymer containing about 0 mol percent to about 20 mol percent of polymerized lactide, and about 80 mol percent to about 100 mol percent of polymerized glycolide. The second absorbable polymeric component is a glycolide polymer or a lactide/glycolide copolymer containing about 0 mol percent to about 20 mol percent of polymerized lactide, and about 80 mol percent to about 100 mol percent of polymerized glycolide.

Another aspect of the present invention is a thermally processed absorbable polymer blend composition. The polymer blend has a first absorbable polymer component and a second absorbable polymer component. Wherein, the first polymeric component has a weight average molecular weight higher than the weight average molecular weight of the second polymeric component, and wherein at least one of said components is at least partially end-capped by a carboxylic acid group.

Yet another aspect of the present invention is a novel absorbable medical device. The medical device comprises an absorbable polymer blend of a first absorbable polymer component and a second absorbable polymer component. Wherein, the first polymeric component has a weight average molecular weight higher than the weight average molecular weight of the second polymeric component, and wherein at least one of said components is at least partially end-capped by a carboxylic acid group.

Still yet another aspect of the present invention is a method of manufacturing a medical device. The method includes the steps of processing an absorbable polymer blend. The polymer blend has a first absorbable polymer component and a second absorbable polymer component. Wherein, the first polymeric component has a weight average molecular weight higher than the weight average molecular weight of the second polymeric component, and wherein at least one of said components is at least partially end-capped by a carboxylic acid group.

Further aspects of the present invention include the above-described medical device and method, wherein the polymer blend is thermally processed. The blend can be made by thermal processes and articles can be made from the blend by thermal processes.

These and other aspects and advantages of the present invention will become more apparent from the following description and accompanying drawings.

DETAILED DESCRIPTION OF THE INVENTION

Figure 1A:
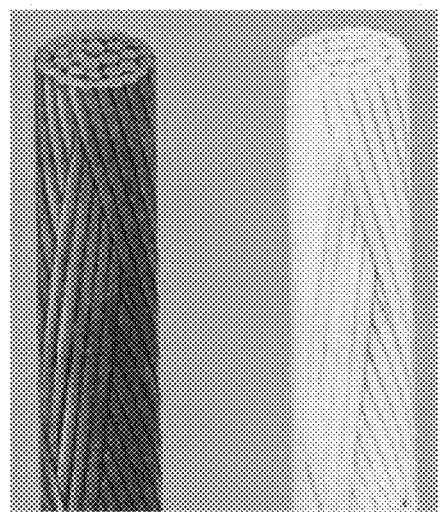
FIGS. 1A-1D illustrate various braided suture constructions.
Figure 1B:
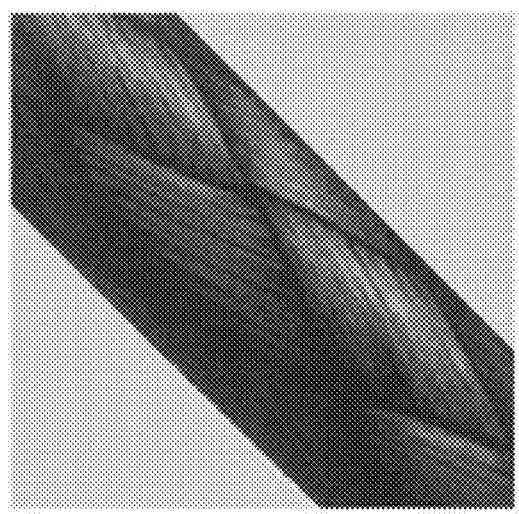
Figure 1C:
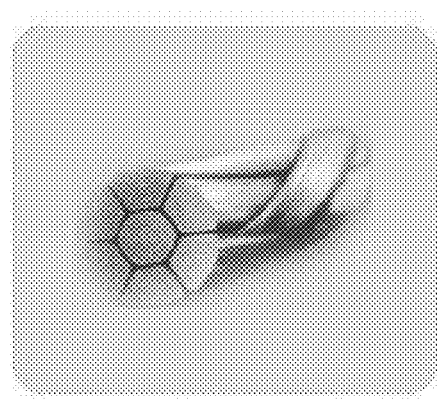
Figure 1D:
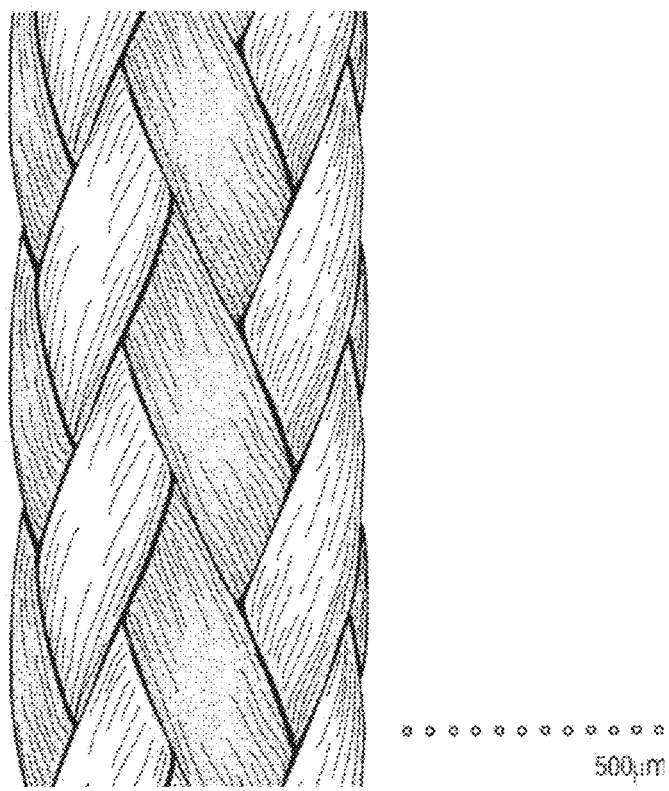

It should be clear to one having ordinary skill in the art that acid level might be expressed by a variety of methods. These include milliequivalents per gram (meq/gram). We intend to define the concept of an acid level to be used herein. One determines the number of moles of carboxylic acid groups attached to the chains of the resin under consideration. If the resin is a polylactone, one determines the number of moles of lactone monomer incorporated into said resin. The acid level is herein defined as the number of moles of said carboxylic acid groups attached to the chains, divided by the number of moles of said lactone monomer incorporated into said resin. In the case of resins containing polymeric repeat units not formed from lactones, the number of moles of repeat units will be included.

Thus if a resin was formed containing 90 moles of polymerized glycolide and 10 moles of polymerized lactide, and had end groups corresponding to 1.7 moles of carboxylic acid groups, one could calculate that the resin had an acid level of 1.7 percent [100×1.7/(90+10)=1.7]. In another example, if a resin was formed containing 81 moles of polymerized glycolide, 9 moles of polymerized lactide, and 10 moles of repeat units of hexamethylene adipate, and had end groups corresponding to 2.0 moles of carboxylic acid groups, one could calculate that this second resin had an acid level of 2.0 percent [100×2.0/(81+9+10)=2.0].

For a surgical suture based on a polyglycolide or a glycolide-rich copolymer, the minimum acid level is 0.3 percent and the maximum acid level that can be incorporated and still allow high mechanical properties is dependent on the molecular weight of the lower molecular weight blend component. When the lower molecular weight component is blended with a higher molecular weight blend component possessing a weight average molecular weight of 80,000 Daltons, the maximum acid level limit is approximately 12 percent when the initiator ratio for the lower molecular weight blend component value, $IR_2$, is 10; when $IR_2$ is 20, the maximum acid level limit is approximately 6 percent.

We have determined that when the lower molecular weight component is blended with a higher molecular weight blend component possessing a weight average molecular weight of 80,000 Daltons, the maximum acid level limit as a function of the initiator ratio for the lower molecular weight blend component value, $IR_2$, can be described by the following expression:

$$\text{Max acid level} = 110 \times IR_2^{-0.983} \quad (1)$$

We have determined that when the lower molecular weight component is blended with a higher molecular weight blend component possessing a weight average molecular weight of 120,000 Daltons, the maximum acid level limit as a function of the initiator ratio for the lower molecular weight blend component value, $IR_2$, can be described by the following expression:

$$\text{Max acid level} = 140 \times IR_2^{-0.994} \quad (2)$$

The initiator ratio, IR, is defined as the ratio of moles of initiator divided by the total moles of monomers. $IR_1$ refers to the initiator ratio of the first blend component and $IR_2$ refers to the initiator ratio of the second blend component.

In some embodiments of the present invention, $IR_1$ values can range from about 250 to about 1200 and $IR_2$ values can range from about 8 to about 100.

Thus the maximum amount of acid that can be incorporated into the novel blends of the present invention is dependent on the $IR_2$ value, as well as the molecular weight of the higher molecular weight blend component. So when the value of $IR_2$ is 10, the maximum acid value is about 12 percent when the weight average molecular weight of the high molecular weight component is 80,000 Daltons, is about 14 percent when the weight average molecular weight of the high molecular weight component is 120,000 Daltons. Correspondingly, when the value of $IR_2$ is 20, the maximum acid value is about 6 percent when the weight average molecular weight of the high molecular weight component is 80,000 Daltons, is about 7 percent when the weight average molecular weight of the high molecular weight component is 120,000 Daltons.

With lower values of $IR_2$, higher a maximum acid levels are possible. For instance, maximum acid levels of about 20 percent when the first polymeric component has a weight average molecular weight of 80,000 Daltons, and wherein the maximum acid level is about 26.5% when the first polymeric component has a weight average molecular weight of 120,000 Daltons.

The novel polymer blends of the present invention are made from absorbable polyester (co)polymers and (co) oligomers. Preferably, one of the blend components is a glycolide/lactide co-polymer. Another blend component is a glycolide/lactide co-oligomer with a substantial number of endgroups acidic in nature.

The glycolide/lactide copolymer will be manufactured in a conventional manner. A preferred manufacturing method is as follows. Lactone monomers are charged along with an alcohol initiator, a suitable catalyst, and dye if desired, into a conventional stirred pot reactor. After purging to remove oxygen, under a nitrogen atmosphere, the reactants are heated with agitation to conduct a ring-opening polymerization. After a suitable time the formed resin is discharged and sized appropriately. The resin particles are subjected to a devolatilization process and are subsequently stored under vacuum. The mole percent of polymerized glycolide and polymerized lactide in the glycolide-rich co-polymer useful in the novel blends of the present invention may be varied to provide desired characteristics. Typically, the mole percent of polymerized glycolide in the glycolide-rich polymer will be about 80 percent to about 100 percent, more typically about 85 percent to about 95 percent, and preferably about 88 percent to about 92 percent. When the polymerized glycolide in the glycolide-rich polymer is 100 percent, the polymer is polyglycolide; polyglycolide is preferred for some surgical applications. Typically, the mole percent of polymerized lactide in the glycolide-rich co-polymer will be about 0 percent to about 20 percent, more typically about 5 percent to about 15 percent, and preferably about 8 percent to about 12 percent.

Table 1 describes parameters and ranges for the novel polymer blends of the present invention. Throughout this application, $IV_1$ refers to the inherent viscosity of blend component 1, $IV_2$ refers to the inherent viscosity of blend component 2, $IV_{BLEND}$ refers to the inherent viscosity of the blend. Similarly, $M_{w1}$ refers to the weight-average molecular weight of blend component 1, $M_{w2}$ refers to the weight-average molecular weight of blend component 2, $M_{wBLEND}$ refers to the weight-average molecular weight of the blend and $M_{wFIBER}$ refers to the weight-average molecular weight of the fiber. Inherent viscosity measurements were made at a concentration of approximately 0.1 g/dL at 25° C. in hexafluoroisopropanol (HFIP).

TABLE 1

| Factor | Dimensions | Minimum Value | Preferred Operating Range | Max Value |
| --- | --- | --- | --- | --- |
| $IV_1$ | dL/g | 0.9 | 1.4 to 1.7<br>Preferred: 1.45 to 1.55 | 2.5 |
| $IV_2$ | | 0.1 | 0.20 to 0.25<br>Preferred: 0.22 to 0.23 | 0.65 |
| $IV_{BLEND}$ | | 0.8 | 1.1 to 1.4<br>Most Often Observed: 1.15-1.25 | 2 |
| $IV_{FIBER}$ | | 0.5 | 0.90 to 1.05<br>Most Often Observed: 0.95 to 1.0 | 1.8 |
| $M_{w1}$ | Daltons | 42,000 | 75,000 to 100,000<br>Most Often Selected: 80,000 to 90,000 | 175,000 |
| $M_{w2}$ | | 1,400 | 4,700 to 5,200<br>Most Often Selected: 4,800 to 5,000 | 24,000 |
| $M_{wBLEND}$ | | 35,000 | 55,000 to 75,000<br>Most Often Observed: 58,000 to 65,000 | 120,000 |
| $M_{wFIBER}$ | | 18,000 | 40,000 to 55,000<br>Most Often Observed: 42,000 to 46,000 | 100,000 |
| Acid Levels | Percent | 0.3 | 1.2 to 2.2<br>Most Often 1.7 | 23, when blended with a resin with an $M_w$ of 80k Daltons[1]<br>28, when blended with a resin with an $M_w$ of 120k Daltons[1] |
| Weight Percent of Low MW Component | Percent | 1.25<br>(assuming an $IR_2$ of 5) | 12 to 22<br>(using an $IR_2$ of 20) | Approximately 50 weight percent[1] |

[1]Maximum acid levels depend on the particular application (suture, etc.), the $M_w$ of the high molecular weight component, AND on the value of $IR_2$
(2) Although $IV_{FIBER}$, and $M_{wFIBER}$ are listed in TABLE 1, these designators would apply to any medical device made from the inventive polymeric blends, not just fibers We have found that the polymers of the present invention can be made utilizing metal-based catalysts such as tin catalysts or titanium catalysts. Tin catalysts include stannous octoate and stannous chloride. We have additionally found that the level of catalyst is advantageously in the range of about 3 to 30 ppm, based on the metal content.

The respective amounts of the higher and lower molecular weight polymeric components present in the novel blends of the present invention will be sufficiently effective to provide the desired characteristics and properties. The novel absorbable polymeric blends of the present invention will typically contain about 1.25 wt. % to about 50 wt. % of the lower molecular weight component, more typically about 12 wt. % to about 22 wt. %. The higher molecular weight component will typically make up the remainder of the blends.

In some instances, articles can be made directly from the blend components by thermal processes; example of this include direct melt extrusion of a physical mixture of the blend components or direct injection molding of a physical mixture of the blend components. To be clear, a physical mixture of the blend components is introduced to the supply hopper of the forming equipment, extruder, injection molder, etc.

Four individual blends of the subject invention were made and converted into yarns via multifilament extrusion, and orientation. The yarns were further processed into size 2/0 braids. The four blends were made to have an acid level of 1.7 percent, similar to what is described in the Examples. The braids were coated to provide lubricity and a relevant amount of triclosan antibacterial agent; the coated braids were sterilized by ethylene oxide (EO).

Inherent viscosity measurements of the polymer blends and the tenacities of the yarns made therefrom, as well as molecular weight data as collected from gel permeation chromatography (GPC) and IV measurements made on the corresponding braids are summarized in Tables 10 to 12. Throughout this application, $M_w$ refers to the weight-average molecular weight, $M_n$ refers to the number-average molecular weight and $M_z$ refers to the z-average molecular weight.

The GPC samples were dissolved in hexafluoro-isopropanol (HFIP) at approximately 2 mg/ml. After all the solid was dissolved, each solution was filtered by a 0.45 µm filter disk into a GPC vial for analysis. The GPC/MALLS system used for the analysis comprised a Waters 2695 HPLC, a Wyatt Optilab rEX Refractometer, and a Wyatt HELEOS II Multi-angle Laser Light Scattering Detector. Two PL HFIP-gel columns (9 µm, 300 mm×7.5 mm i.d.) from Polymer Laboratories were used for separation. The column temperature was set at 40° C. HFIP with 0.01M Lithium Bromide (LiBr) (0.2% v/v H2O) was used as the mobile phase and was delivered at a constant flow rate of 0.7 ml/min. The injection volume was 70 µl. Both Empower (Waters) and Astra (Wyatt) software were used for instrument operation and data analysis.

Molecular weight data as collected from GPC and inherent viscosity measurements for the above braids after EO sterilization are shown below in Table 12.

The polyglycolide homopolymer or the glycolide-rich glycolide/lactide copolymer may be characterized by chemical analysis. These characteristics include, but are not limited to, an inherent viscosity range from about 0.8 about 2 dL/g, as measured in hexafluoroisopropanol (HFIP) at 25° C. and at a concentration of 0.1 g/dL for resin of the inventive polymer blend. Gel permeation chromatography analysis showed a weight average molecular weight range from approximately 35,000 to 120,000 Daltons. It is to be understood that higher molecular weight resins can be employed, provided the processing equipment used to form the blend and to form the medical device are capable of handling the melt viscosities inherent to these higher molecular weights, and may be desirable for certain applications. For example, in some applications, a resin with an inherent viscosity of 2.5 dL/g may be needed to produce medical devices requiring certain characteristics, such as higher strength. The novel polymer blends of the present invention will typically have a melting transition from approximately 185 to 224° C., a glass transition temperature range of about 35° C. to about 45° C., and a crystallinity level of about 30 to about 50 percent.

Nuclear magnetic resonance analysis confirmed that the dried co-polymeric resin is a random copolymer of glycolide and lactide. It is to be understood that different isomers of lactide can be used, such as L(−)-lactide or D(+)-lactide or meso-lactide.

The characteristics of the polymer blends of the present invention will be sufficiently effective to provide the needed physical properties to allow the surgical devices to function as intended, yet lose these mechanical properties at a rate much quicker than convention synthetic absorbable polymers of like composition.

For the purpose of this application we wish to define the term of capping or end-capping. Capping or end-capping is the chemical modification of the polymer chain termini. These terms also refer to the chemical modification of the chain termini of low molecular weight polymers or oligomers. For clarification purposes let us consider ring-opening polymerization where one starts with an initiator and lactone monomers. Let us first consider a monofunctional alcohol initiator such as 1-dodecanol. In this case the resulting polymer chains have an alkyl functionality on one end and an alcoholic functionality on the other. One can now chemically modify the alcoholic functionality into a carboxylic functionality. This can be conveniently accomplished by reaction of the alcohol chain end with a cyclic anhydride, such as diglycolic anhydride or succinic anhydride. For the purposes of this application we can describe this polymer to be end-capped with a carboxylic acid functionality.

Similarly, one could consider using an initiator containing both a carboxylic acid functionality and an alcohol group, such as glycolic acid. In this case the resulting polymer chains have a carboxylic acid functionality on one end and an alcoholic functionality on the other. One can now again chemically modify the alcoholic functionality into a carboxylic acid functionality. For the purposes of this application we can describe this polymer to be end-capped with a carboxylic acid functionality. To be clear, we do not consider the glycolic acid initiated polymer to be end-capped until its end is converted into a carboxylic acid, for example by further reaction with a cyclic anhydride.

Finally, one could consider using an initiator containing two alcohol functionalities, such as diethylene glycol. In this case the resulting polymer chains have alcoholic functionalities on both ends. One can now chemically modify both alcoholic functionalities into carboxylic acid functionalities. For the purposes of this application we can describe the latter two polymers to be end-capped with a carboxylic acid functionality.

It should be clear to those having ordinary skill in the art that the capping can be achieved in multiple ways. These could include also for example direct oxidation of the chain ends.

In one embodiment of the present invention, the percentage of end-capping of the novel absorbable polymer blend with carboxylic acid groups is at least 25 percent. In another embodiment of the present invention, the percentage of end-capping of the novel absorbable polymer blend with carboxylic acid groups for the first polymeric component is from about 0 to about 100%, and the percentage of end-capping with carboxylic acid groups for the second polymeric component is from about 25% to about 100%.

In one embodiment of the present invention the polymer blend contains a conventional dye. The dye should be one acceptable for clinical use; this includes, without limitation, D&C Violet No. 2 and D&C Blue No. 6 and similar combinations thereof. It should be noted that one or more of the blend components may be dyed or the dye can be introduced during the blend compounding stage. Additionally, in another embodiment, one polymeric component of the blend might be colored with a first dye at a given concentration, and the second polymeric component colored with the same or another dye at the same or another concentration.

The novel polymer blends of the present invention can be manufactured from the individual components using a variety of conventional processes using conventional processing equipment. Examples of manufacturing processes include chemical reactions of the ring-opening and polycondensation type, devolatilization and resin drying, dry blending in a tumble dryer, solution blending, extrusion melt-blending, injection molding, thermal annealing, and ethylene oxide sterilization processes. An alternate to dry blending with subsequent melt blending of the mixture may include the use of two or more conventional feeders, preferably loss-inweight feeders, that supply the components to be blended to an extruder; the extruder can be of the single screw or twin screw variety.

Alternately, multiple extruders can be used to feed melts of the blend components, such as in co-extrusion. The novel polymer blends of the present invention may be made using conventional thermal processes. Examples of thermal processes to produce the polymer blends of the present invention include melt blending in an extruder, which can include twin screw blending or single screw extrusion, co-extrusion, twin screw blending with simultaneous vented-screw vacuum devolatilization, vacuum tumble drying with thermal devolatilization, monomer removal by solvent extraction at elevated temperature, and resin annealing.

The polymer components, as well as blends of the subject invention can be sized by conventional means such as pelletization, granulation, and grinding.

A further embodiment of the present invention would be feeding appropriately sized particles of the blend components directly to the hopper of the extruder or the injection molding machine. It would be possible for one skilled in the art to apply this technique to other processing methodologies, such as, but not limited to, film or fiber extrusion. Limiting the thermal history of the polymer blend components is advantageous in that it avoids the possibility of premature degradation. Additional methods of thermal processing can include a process selected from the group consisting of injection molding, compression molding, blow molding, blown film, thermoforming, film extrusion, fiber extrusion, sheet extrusion, profile extrusion, melt blown nonwoven extrusion, co-extrusion, tube extrusion, foaming, rotomolding, calendaring, and extrusion. As noted earlier, appropriately sized particles of the blend components can be blended in the melt using these thermal processing means. In some cases it may be possible and desirable to use solution processing techniques, such as solution spinning, gel spinning and electro spinning.

Other examples of conventional manufacturing process equipment that may be used to manufacture the novel polymer blends of the present invention may include single-screw and twin-screw compounders that operate on a continuous basis or batch-style compounders.

The equipment will be sufficiently sized to effectively and provide the desired batch size. Examples of such equipment include chemical reactors ranging in size, for example, from two-gallon to seventy-five gallon or more in capacity, process devolatilization dryers ranging, for example, from one cubic feet to twenty cubic feet or more, single and twin-screw extruders ranging, for example, from about one inch to about three inches in diameter, and injection molders ranging, for example, from about seven to about 40 tons or more in size. A preferred method and associated equipment for manufacturing the polymer blends of the present invention can be found in Examples 7 to 9.

If desired, the polymer blends of the present invention may contain other conventional components and agents. The other components, additives or agents will be present to provide additional desired characteristics to the polymer blends and medical devices of the present invention including antimicrobial characteristics, controlled drug elution, radio-opacification, and enhanced osseointegration.

Such other components will be present in a sufficient amount to effectively provide for the desired effects or characteristics. Typically, the amount of the other adjuncts will be about 0.1 weight percent to about 20 weight percent, more typically about 1 weight percent to about 10 weight percent and preferably about 2 weight percent to about 5 weight percent based on the total weight of the blend.

The variety of therapeutic agents that can be used in the polymer blends of the present invention is vast. In general, therapeutic agents which may be administered via compositions of the invention include, without limitation, antiinfectives, such as antibiotics and antiviral agents.

Such other components will be present in a sufficient amount to effectively provide for the desired effects or characteristics. Typically, the amount of the other adjuncts will be about 0.1 weight percent to about 20 weight percent, more typically about 1 weight percent to about 10 weight percent and preferably about 2 weight percent to about 5 weight percent.

Examples of antimicrobial agents include the polychloro phenoxy phenols such as 5-chloro-2-(2,4-dichlorophenoxy) phenol (also known as Triclosan). Examples of radio-opacification agents include barium sulfate while examples of osseointegration agents include tricalcium phosphate.

The variety of therapeutic agents that can be used in the polymer blends of the present invention is vast. In general, therapeutic agents which may be administered via pharmaceutical compositions of the invention include, without limitation, antiinfectives, such as antibiotics and antiviral agents; analgesics and analgesic combinations; anorexics; antihelmintics; antiarthritics; antiasthmatic agents; adhesion preventatives; anticonvulsants; antidepressants; antidiuretic agents; antidiarrheals; antihistamines; anti-inflammatory agents; antimigraine preparations; contraceptives; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; tranquilizers; naturally derived or genetically engineered proteins, polysaccharides, glycoproteins, or lipoproteins; oligonucleotides, antibodies, antigens, cholinergics, chemotherapeutics, hemostatics, clot dissolving agents, radioactive agents and cystostatics. Therapeutically effective dosages may be determined by in vitro or in vivo methods. For each particular additive, individual determinations may be made to determine the optimal dosage required. The determination of effective dosage levels to achieve the desired result will be within the realm of one skilled in the art. The release rate of the additives may also be varied within the realm of one skilled in the art to determine an advantageous profile, depending on the therapeutic conditions to be treated.

Suitable glasses or ceramics include, but are not limited to phosphates such as hydroxyapatite, substituted apatites, tetracalcium phosphate, alpha- and beta-tricalcium phosphate, octacalcium phosphate, brushite, monetite, metaphosphates, pyrophosphates, phosphate glasses, carbonates, sulfates and oxides of calcium and magnesium, and combinations thereof.

The novel absorbable medical devices of the present invention that are made from the novel absorbable polymer blends of the present invention include, but are not limited to, conventional medical devices, especially fibrous devices such as monofilament-based and multifilament-based sutures and meshes, woven fabrics, nonwoven fabrics, knitted fabrics, fibrous bundles, cords, and other implantable medical devices, including staples, tacks, clips, tissue fixation devices, mesh fixation devices, anastomotic devices, suture anchors and bone anchors, tissue and bone screws, bone plates, prostheses, support structures, tissue augmentation devices, tissue ligating devices, patches, substrates, tissue engineering scaffolds, composites, bone grafts, drug delivery devices, stents, bone waxes and bone fillers, combinations and equivalents.

Figure 2:
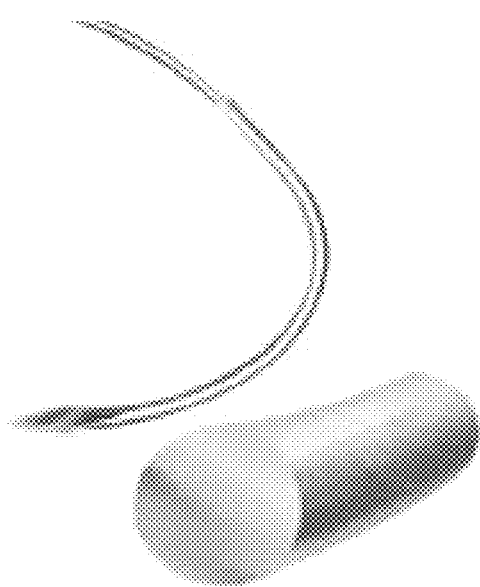
FIG. 2 is an illustration of a monofilament suture alongside a surgical needle.
Figure 3:
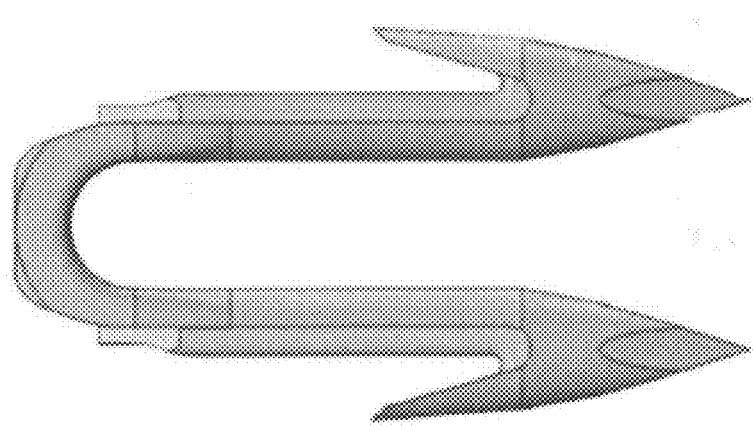
FIG. 3 is an illustration of a molded surgical tack.
Figure 4:
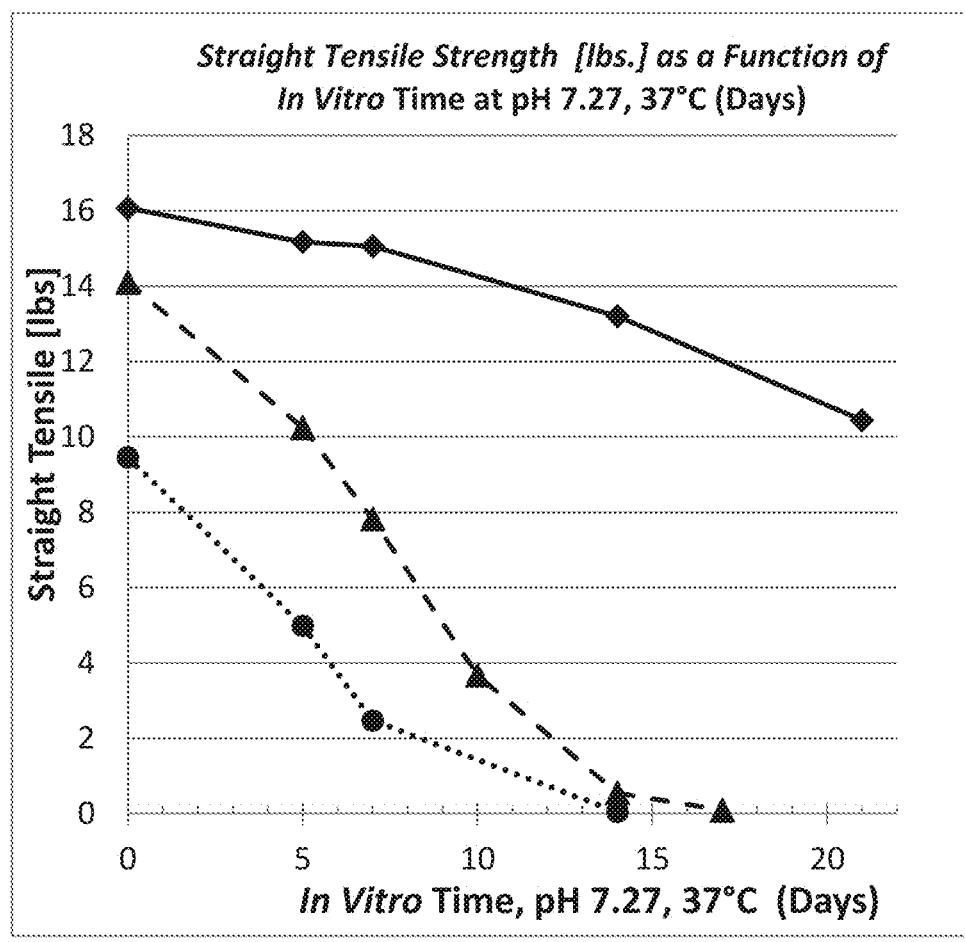
FIG. 4 is a plot of breaking strength as a function of implantation time for a normally absorbing prior art poly(lactide-co-glycolide) multifilament suture, a prior art rapidly absorbing poly(lactide-co-glycolide) multifilament suture, and a rapidly absorbing poly(lactide-co-glycolide) multifilament suture of the present invention.
Figure 5:
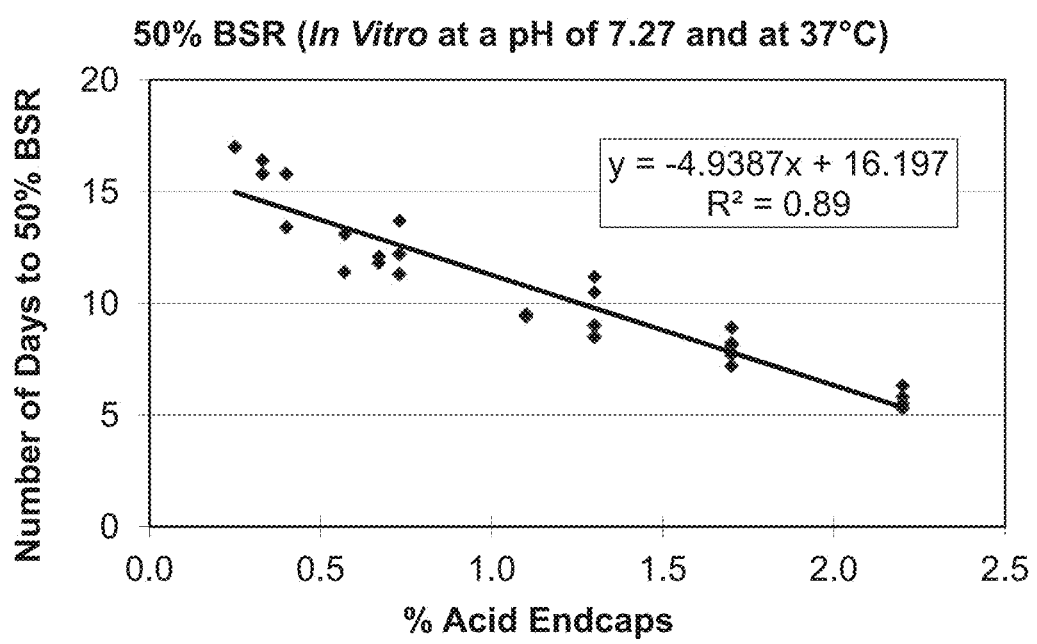
FIG. 5 is a plot of the time required in an aqueous buffer at a pH of 7.27 and 37 degree centigrade for a poly(lactide-co-glycolide) multifilament suture to achieve a drop in initial breaking strength of 50 percent, as a function of the acid level present.
Figure 6:
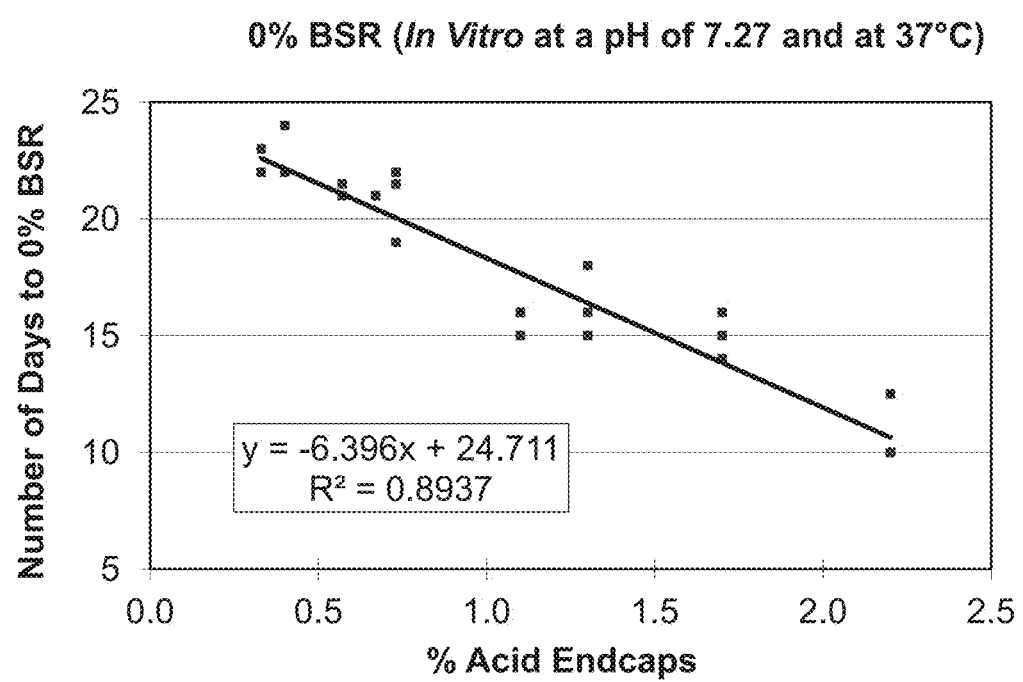
FIG. 6 is a plot of the time required in an aqueous buffer at a pH of 7.27 and 37 degree centigrade for a poly(lactide-co-glycolide) multifilament suture to achieve a drop in initial breaking strength of 100 percent, as a function of the acid level present.
Figure 7:
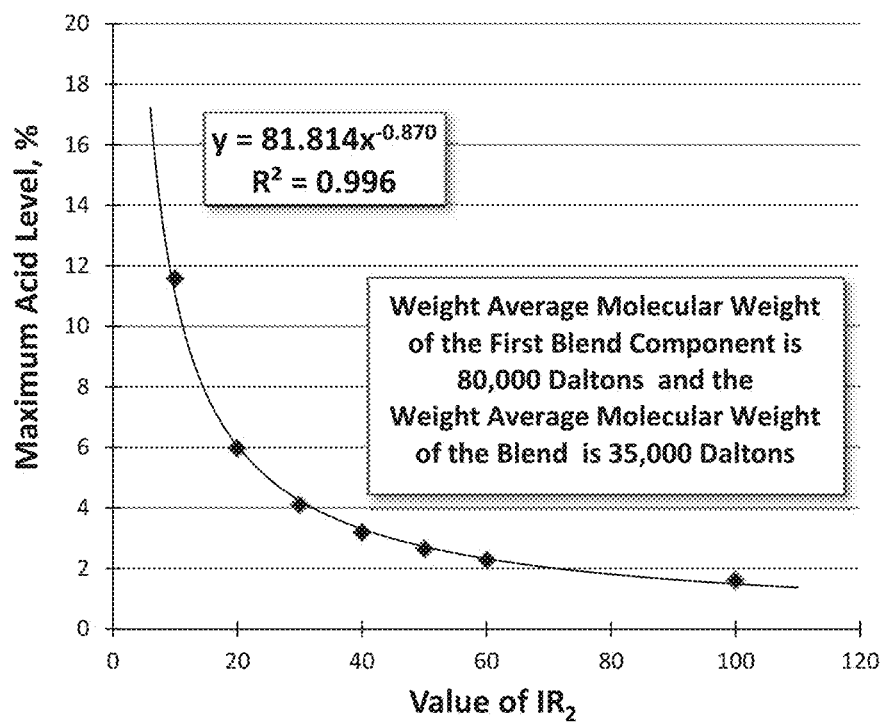
FIG. 7 is a plot of maximum acid level vs. the value of $IR_2$.

Referring to FIGS. 1A-D, illustrations of conventional braided surgical sutures that can be made from the novel absorbable polymer blends of the present invention are seen. The sutures are seen to be made or braided from filaments or multifilament yarns, and the sutures may have a core construction. An illustration of a conventional monofilament suture that can be made from the novel absorbable polymer blends of the present invention alongside of a conventional surgical needle is seen in FIG. 2. A surgical tack that can be molded from the novel absorbable polymer blends of the present invention is illustrated in FIG. 3.

For purposes of this application, we wish to use the term suture to mean surgical sutures, and more broadly fibrous devices, including monofilament and multifilament yarns used in the medical field. These include, but are not limited to, fibers used to make surgical meshes; fibers used to make surgical fabrics and tapes made by any known method of processing (knitted, woven, nonwoven, etc). The sutures of the present invention may be used for a variety of applications including, but not limited to wound fixation, wound closure, general tissue approximation, and attachment of implants.

Modern surgical sutures generally range from Size 5 (heavy braided suture for orthopedics) to Size 11/0 (for example, a fine monofilament suture for ophthalmics). The actual diameter of thread for a given U.S.P. size differs depending on the suture material class. The diameters of sutures in the synthetic absorbable suture class are listed in the United States Pharmacopeia (USP) as well as in the European Pharmacopoeia. The USP standard is more commonly used.

We have found that the polymeric blends of the present invention may be used to produce sterile surgical sutures possessing significant initial breaking strength, which then possess little or no mechanical strength after 14 days post-implantation, and absorb in about 42 days post-implantation. These inventive sutures of a given size (diameter) possess as much initial breaking strength as a suture one size larger of presently available sterile, fast-absorbing, commercial sutures that lose most of their breaking strength at 14 days post-implantation and are substantially absorbed in about 42 days.

The polymeric components of the medical devices of the present invention will have an inherent viscosity of at least about 0.5 dL/g as measured in hexafluoroisopropanol at 25° C. at a concentration of 0.1 g/dL, provided the medical device is fully soluble in this solvent.

Injection Molding

Injection molding is a process well-known in the plastic industry. It is designed to produce parts of various shapes and sizes by melting the plastic, mixing and then injecting the molten resin into a suitably shaped mold. After the resin is solidified, the part is generally ejected from the mold and the process continued.

For the purposes of this invention, a conventional 30-ton electrically controlled injection molding machine can be used. The polymer blends of the present invention can be processed in the following general manner. The polymer and polymer blends can be fed by gravity from a hopper, under nitrogen purge, into a heated barrel. The polymer will generally move forward in the barrel by the screw-type plunger into a heated chamber. As the screw advanced forward, the molten polymer and polymer blends will be forced through a nozzle that rests against a mold, allowing the polymer and polymer blends to enter a specially designed mold cavity, through a gate and runner system. The blend will be formed into the part in the mold cavity, and then allowed to cool at a given temperature for a period of time. It will be then removed from the mold, or ejected, and separated from the gate and runner.

A further aspect of the present inventive polymer blends is the persistence of weight-average molecular weight upon thermal processing. A benefit of having the weight-average molecular weight not change much during thermal processing, such as melt extrusion, is the enabling of higher mechanical properties in the fabricated devices so produced. We have found that in the case of producing multifilament yarns, a minimum weight-average molecular weight of about 35,000 Daltons in the yarns is desirable. If the weight-average molecular weight of the polymer blend drops too much during thermal processing, it would be difficult to achieve a minimum weight-average molecular weight in the resulting medical device, and hence, allowing the part to possess the minimum desired mechanical properties.

An additional further aspect of the present inventive absorbable polymer blends is the incorporation of a third polymeric component, wherein said third polymeric component is selected from the group consisting of non-absorbable polymers, rapidly absorbing polymers, and slowly absorbing polymers.

It is to be noted that the present inventive polymeric blends allow for the manufacture of inventive medical devices that can comprise an antimicrobial agent such as triclosan. Of particular interest are surgical sutures treated with this antimicrobial agent. Presently available sterile, fast-absorbing, commercial sutures that lose most of their breaking strength at 14 days post-implantation and are substantially absorbed in about 42 days are not treated with triclosan. Attempts to produce such a suture comprising triclosan are fraught with processing difficulties. Using the inventive polymer blends described herein, we have been able to produce sterile surgical sutures treated with triclosan that lose most of their breaking strength at 14 days post-implantation and are substantially absorbed in about 42 days.

Another aspect of the present invention is a suture having an absorption time at least 20% shorter than the absorption time of a similar suture consisting essentially of the first polymeric component. Yet another aspect is a suture having a post-implantation time required to achieve zero mechanical strength at least 30% shorter than the post-implantation time required to achieve zero mechanical strength for a similar suture consisting essentially of the first polymeric component. Yet another aspect is a suture having a pre-implantation strength greater than or equal to 75% of the pre-implantation strength of a similar suture consisting essentially of the first polymeric component.

The following examples are illustrative of the principles and practice of the present invention, although not limited thereto.

Example 1

Synthesis of Uncapped, Dodecanol Initiated at IR 800, 16 PPM Tin, 90/10 Poly(L(-)-Lactide-Co-Glycolide)

Into a suitable 50-gallon stainless steel oil jacketed reactor equipped with agitation, 24.66 kg of L(-)-lactide and 175.34 kg of glycolide were added along with 391.89 g of dodecanol and 74.24 g of a 0.33M solution of stannous octoate in toluene. The reactor was closed and a purging cycle, along with agitation at a rotational speed of 13 RPM in an upward direction, was initiated. The reactor was evacuated to pressures less than 2 Torr, and was held at this condition for at least 15 minutes, followed by the introduction of nitrogen gas. The vacuum-nitrogen purge cycle was repeated once more to ensure a dry atmosphere.

At the end of the final introduction of nitrogen, the pressure was adjusted to be slightly above one atmosphere. The heating oil temperature was raised to 135° C. When the batch temperature reached 120° C., the agitator was stopped and restarted in the downward direction at 13 rpm.

The vessel was heated by computer control at a various rates, depending on the batch temperature and the temperature difference between the oil jacket and batch, $T_0-T_B$.

For the batch temperature interval from room temperature up to 199° C., for $T_0-T_B$ equal or smaller than 3° C., the heating rate was 42° C. per hour, and for $T_0-T_B$ greater than 3° C., the heating rate was 24° C. per hour. When the batch temperature reached 170° C., the agitator speed was reduced to 6 RPM. When the batch molten mass reached 200° C. the reaction continued for an additional 100 minutes. The oil temperature was ramped up at an average rate of 30° C. per hour and remained at 199-205° C.

At the end of the reaction period, the oil temperature was increased to 212° C., and the polymer was discharged from the vessel, by means of a polymer melt pump, into an underwater pelletizer. During pelletization, the pelletized polymer was transferred to a centrifugal dryer where oversized material was separated at the agglomerate catcher chute. The pelletization cutter speed was adjusted to give an average pellet weight of 25 mg.

The polymer pellets were transferred to a 20 cubic foot stainless steel rotary vacuum dryer. The dryer was closed and the pressure was reduced to less than 200 mTorr. Once the pressure was below 200 mTorr, tumbler rotation was activated at a rotational speed of 6 RPM and the batch was vacuum conditioned for a period of 18 hours. After the 18 hour vacuum conditioning, the oil temperature was set to a temperature of 110° C., for a period of 24 hours. At the end of this heating period, the batch was allowed to cool for a period of at least 4 hours, while maintaining rotation and high vacuum. The polymer was discharged from the dryer by pressurizing the vessel with nitrogen, opening the slide-gate, and allowing the polymer granules to descend into waiting vessels for long term storage.

The long term storage vessels were air tight and outfitted with valves allowing for evacuation so that the resin is stored under vacuum. The resin was characterized. It exhibited an inherent viscosity of 1.53 dL/g, as measured in hexafluoroisopropanol at 25° C. and at a concentration of 0.10 g/dL. Gel permeation chromatography analysis showed a weight average molecular weight of approximately 82,600 Daltons. Differential scanning calorimetry revealed a glass transition temperature of 45° C. and a melting transition at 197° C. Nuclear magnetic resonance analysis confirmed that the resin was a random copolymer of polymerized L(-)-lactide and glycolide. X-ray diffraction analysis showed a crystallinity level of approximately 37.6 percent.

Example 2

In a manner similar to Example 1, a synthesis was conducted to prepare an dodecanol initiated, 90/10 poly(L(-)-lactide-co-glycolide) copolymer. It exhibited a similar inherent viscosity as the copolymer of Example 1. The copolymer of this Example 2 was converted into an inventive polymer blend, which was then subsequently extruded and processed into braided suture materials, which were then utilized for in vivo testing.

Example 3

Synthesis of Capped, IR 600, 6.6 PPM Tin, 90/10 Poly(L(-)-Lactide-Co-Glycolide)

Into a suitable 10-gallon stainless steel oil jacketed reactor equipped with agitation, 3.080 kg of L(-)-lactide and 21.919 kg of glycolide were added along with 26.64 g of glycolic acid and 4.25 ml of a 0.33M solution of stannous octoate in toluene. The reactor was closed and a purging cycle, along with agitation at a rotational speed of 7 RPM in an upward direction, was initiated. The reactor was evacuated to pressures less than 200 mTorr, and was held at this condition for at least 15 minutes, followed by the introduction of nitrogen gas. The cycle was repeated two times to ensure a dry atmosphere.

At the end of the final introduction of nitrogen, the pressure was adjusted to be slightly above one atmosphere. The heating oil temperature was raised to 130° C. at an average heating rate of 120° C./hour. When the batch temperature reached 120° C., the agitator was stopped and restarted in the downward direction at 7 rpm.

The heating oil controller was set at 203° C. at an average heating rate of 60° C. per hour. When the batch molten mass reached 200° C., the reaction was continued for an additional 5 hours at 7 RPM.

The agitator was stopped and the reactor was placed under a slight nitrogen purge with open venting. The charging port was opened and 40.66 grams of diglycolic anhydride was added to the reaction mass. The reactor port was closed. Venting and nitrogen purging were stopped. Agitation was resumed at 7 rpm and the reaction was continued for an additional hour at an average oil heating temperature of 202° C.

At the end of the reaction period, the polymer was discharged from the vessel into aluminum trays and was stored in a freezer. The polymer was ground and was screened through a 3/16" screen, and it was dried in a three cubic foot rotary vacuum dryer, at 10 rpm for 18 hours, at room temperature. At the end of the period the vacuum was 50 mTorr, the drying cycle continued for an additional 19 hours under vacuum at 110° C. At the end of this heating period, the batch was allowed to cool for a period of at least 4 hours, while maintaining rotation and high vacuum. The polymer was discharged from the dryer by pressurizing the vessel with nitrogen, opening the slide-gate, and allowing the polymer granules to descend into waiting vessels for long term storage. The resin was characterized. Gel permeation chromatography analysis showed a weight average molecular weight of approximately 65,500 Daltons. Differential scanning calorimetry revealed a glass transition temperature of 39° C. and a melting transition at 201° C. Nuclear magnetic resonance analysis confirmed that the resin was a random copolymer of polymerized L(-)-lactide and glycolide.

Example 4

Synthesis of Dodecanol Initiated, Uncapped, IR 20, 6.6 PPM Tin, 10/90 Oligo(L(-)-Lactide-Co-Glycolide)

Into a suitable 2 gallon stainless steel oil jacketed reactor equipped with agitation, 862.58 grams of L(-)-lactide and 6137.42 grams of glycolide were added along with 548.35 g of dodecanol and 1.19 ml of a 0.33M solution of stannous octoate in toluene. The reactor was closed and a purging cycle, along with agitation at a rotational speed of 7 RPM in an upward direction, was initiated. The reactor was evacuated to pressures less than 220 mTorr, and was held at this condition for at least 15 minutes, followed by the introduction of nitrogen gas. The cycle was repeated once again to ensure a dry atmosphere.

At the end of the final introduction of nitrogen, the pressure was adjusted to be slightly above one atmosphere. The heating oil temperature was raised to 130° C. at an average heating rate of 228° C./hour. When the batch temperature reached 120° C., the agitator was stopped and restarted in the downward direction at 7 RPM.

The heating oil controller was set at 203° C. at an average heating rate of 60° C. per hour. When the batch molten mass reached 200° C. the reaction continued for an additional 2 hours and 25 minutes at 7 rpm. The heating oil controller was set at 205° C. and the reaction continued for an additional 2 hours and 15 minutes.

At the end of the reaction period, the polymer was discharged from the vessel into aluminum trays and was stored in a freezer. The polymer was ground and was screened through a 3/16" screen, and it was stored under vacuum. The resin was characterized.

Gel permeation chromatography analysis showed a weight average molecular weight of approximately 4,550 Daltons and a number average molecular weight of 2,620 Daltons. Differential scanning calorimetry revealed a glass transition temperature of 39° C. and a melting transition at 183° C. for this semi-crystalline polymer. Since the initiator employed in this polymerization did not contain a carboxylic acid group and the resulting reaction product was not end-capped, the expected acid level for this polymer is expected to be close to zero.

Example 5

Synthesis of Capped, IR 20, 6.6 PPM Tin, 10/90 Oligo(L(-)-Lactide-Co-Glycolide)

Into a suitable 2 gallon stainless steel oil jacketed reactor equipped with agitation, 862.58 grams of L(-)-lactide and 6,137.4 grams of glycolide were added along with 223.8 g of glycolic acid and 1.19 ml of a 0.33M solution of stannous octoate in toluene. The reactor was closed and a purging cycle, along with agitation at a rotational speed of 7 RPM in an upward direction, was initiated. The reactor was evacuated to pressures less than 200 mTorr, and was held at this condition for at least 15 minutes, followed by the introduction of nitrogen gas. The cycle was repeated once again to ensure a dry atmosphere.

At the end of the final introduction of nitrogen, the pressure was adjusted to be slightly above one atmosphere. The heating oil temperature was raised to 130° C. at an average heating rate of 120° C./hour. When the batch temperature reached 120° C., the agitator was stopped and restarted in the downward direction at 7 RPM.

The heating oil controller was set at 203° C. at an average heating rate of 60° C. per hour. When the batch molten mass reached 200° C., the reaction was continued for an additional 4 hours and 25 minutes at 7 RPM. The agitator was stopped and 341.58 grams of diglycolic anhydride was added to the reactor. Agitation was continued for 60 minutes at 10 RPM in the downward direction.

At the end of the reaction period, the polymer was discharged from the vessel into aluminum trays and was stored in a freezer. The polymer was ground and was screened through a 3/16" screen, and it was stored under vacuum. The resin was characterized. It exhibited an inherent viscosity of 0.25 dL/g, as measured in hexafluoroisopropanol at 25° C. and at a concentration of 0.10 g/dL. Gel permeation chromatography analysis showed a weight average molecular weight of approximately 5,390 Daltons. Differential scanning calorimetry revealed a glass transition temperature of 34° C. and a melting transition at 197° C.

Nuclear magnetic resonance analysis confirmed that the resin was a random copolymer of polymerized L(-)-lactide and glycolide, with a composition of 7.7 percent polymerized L(-)-lactide, 87 percent polymerized glycolide, 0.1 percent lactide monomer, and 0.6 percent glycolide monomer, and 3.0 percent acid groups resulting from end-capping, as measured on a molar basis. X-ray diffraction analysis showed a crystallinity level of approximately 54.5 percent.

Example 6

Synthesis of Capped, IR 20, 6.6 PPM Tin, 10/90 Oligo(L(-)-Lactide-Co-Glycolide)

In a manner similar to Example 5, a synthesis was conducted to prepare an glycolic acid initiated, 90/10 oligo(L(-)-lactide-co-glycolide) co-oligomer. The resin was characterized; it exhibited an inherent viscosity of 0.25 dL/g, as measured in hexafluoroisopropanol at 25° C. and at a concentration of 0.10 g/dL. Gel permeation chromatography analysis showed a weight average molecular weight of approximately 4,870 Daltons and a number average molecular weight of 2,990 Daltons.

Nuclear magnetic resonance analysis confirmed that the resin was a random copolymer of polymerized L(-)-lactide and glycolide, with a composition of 6.8 percent polymerized L(-)-lactide, 85.9 percent polymerized glycolide, 0.4 percent lactide monomer, and 1.0 percent glycolide monomer, and 4.1 mole percent acid groups resulting from the capping step.

Example 7

Dry Blending, Melt Blending, Pelletizing and Drying of Pellets
The Processing of a Mixture of the Polymer of Example 1 and the Polymer of Example 5 Resulting in a Blend
Dry Blending of the Blend Components Once the glycolide/lactide polymers had been produced by the above described methods in the previous examples, appropriate amounts of these components, in divided form (pellets in Example 1 and ground polymer in Example 5) were combined in a dry blend. These dry blends are produced on a weight basis, depending on the particular application and surgical need. In the present Example, uncapped, dodecanol-initiated at IR 800, 16 PPM tin, 10/90 poly(L(-)-lactide-co-glycolide) at 83 weight percent and the lower molecular weight capped, IR 20, 6.6 PPM tin, 10/90 poly(L(-)-lactide-co-glycolide) of Example 5 at 17 weight percent, were dry blended as described below. This lower molecular weight resin can also be referred to as oligo(L(-)-lactide-co-glycolide).

Into a clean 3-cubic foot Patterson-Kelley dryer, 12.210 kilograms of the pelletized glycolide/lactide copolymer of Example 1 were added, followed by 2.501 kilograms of the polymer granules of Example 5. The dryer was closed, and the vessel pressure was reduced to less than 200 mTorr. The dryer rotation was started at 10 RPM and continued for a minimum period of one hour. The dry blend was then discharged into portable vacuum storage containers, and these containers were placed under vacuum, until ready for the melt blending step. (Note that melt blending is often described as polymer compounding.)

For the purpose of this invention, blends of this type can be produced in a similar manner with different compositions.

Melt Blending (Compounding) and Pelletization

Once the dry blends have been produced and have been vacuum conditioned for at least three days to insure low moisture content, the melt-blending step can begin. A Werner & Pfeidlerer Twin-Screw Extruder, Model ZSK-30, was fitted with screws designed for melt blending, utilizing a vacuum port for purposes of volatilizing residual monomer. The screw design contained several different types of elements, including conveying, compression, mixing and sealing elements. The extruder was fitted with a three-hole die plate. A chilled water bath with water temperature set between 40 and 70° F. was placed near the extruder outlet. A strand pelletizer and pellet classifier was placed at the end of the water bath. The extruder temperature zones were heated to a temperature of 190 to 210° C., and the vacuum cold traps were set to −20° C. The pre-conditioned dry blend granules were removed from vacuum and placed in a twin-screw feed hopper under nitrogen purge. The extruder screws were set to a speed of 225 RPM, and the feeder was turned on, allowing the dry blend to be fed into the extruder at a rate of approximately 0.230 kilograms/minute. Throughput could be adjusted by adjusting the feeder rate as is well known. A feed rate is selected based on a balance of economy and degradation avoidance.

The polymer melt blend was allowed to purge through the extruder until the feed was consistent, at which point the vacuum was applied to the vacuum port. The polymer blend extrudate strands were fed through the water bath and into the strand pelletizer. The pelletizer cut the strands into appropriate sized pellets; specifically, with a diameter of about 2 mm and an approximate length of 3 mm. The pellets were then fed into the classifier. The classifier separated larger and smaller pellets from the desired size, usually a weight of about 13 mg per pellet. This process continued until the entire polymer dry blend was melt blended in the extruder, and formed into substantially uniform pellets. The pellet production rate was approximately 170 grams per minute. Samples were taken throughout the extrusion process and were measured for polymer characteristics such as inherent viscosity, molecular weight and composition. Once the melt-blending process was completed, the weighed, pelletized polymer was placed into a dryer as described below. Alternately, if the drier is not immediately available, the pellets may be placed in polyethylene bags, weighed, and stored in a freezer below −20° C. to await devolatilization of residual monomer.

Drying of Pellets

The polymer melt-blend was placed into a 3-cubic foot Patterson-Kelley dryer, which was placed under vacuum. The dryer was closed and the pressure was reduced to less than 200 mTorr. Once the pressure was below 200 mTorr, dryer rotation was activated at a rotational speed of 10 RPM with no heat for 6 hours. After the 6 hour period, the oil temperature was set to 110° C. The oil temperature was maintained at 110° C. for a period of 12 hours. At the end of this heating period, the batch was allowed to cool for a period of at least 4 hours, while maintaining rotation and vacuum. The polymer melt-blend pellets were discharged from the dryer by pressurizing the vessel with nitrogen, opening the discharge valve, and allowing the polymer pellets to descend into waiting vessels for long term storage. The storage vessels were air tight and outfitted with valves allowing for evacuation so that the resin was storage under vacuum. The resin was characterized. Gel Permeation chromatography analysis revealed a weight average molecular weight of 58,300 Daltons. Differential thermal analysis showed a glass transition temperature, $T_g$ of 46° C. and a melting point of 198° C.

For the purpose of this invention, blends of this type with different compositions can be produced in a similar manner.

Example 8

Dry-Blending, Melt-Blending, Pelletization and Drying of a Comparative Example (Blend of Example 1 and Example 4; 0% Acid)

Dry-Blending

In a manner analogous to Example 7, a dry blend containing 83 weight percent of uncapped, Dodecanol Initiated at IR 800, 16 PPM Tin, 90/10 Poly(glycolide-co-L(−)-lactide) as described in Example 1, and uncapped, IR 20, 6.6 PPM Tin, 90/10 Poly(glycolide-co-L(−)-lactide) as described in Example 4, at 17 weight percent, was dry blended in a clean 3-cubic foot commercially available Patterson-Kelley dryer; 5,000 grams of pellets of the glycolide/lactide copolymer of Example 1 were weighed and added to the dryer. In the same 3-cubic foot dryer, 1024 grams of polymer granules of Example 4 were weighed and added to the dryer. The dryer was closed, and the vessel pressure was reduced to less than 200 mTorr. The rotation was started at 10 RPM and continued for a minimum period of one hour. The dry blend was then discharged into portable vacuum storage containers, and these containers were placed under vacuum, until ready for the next step.

Melt-Blending (Compounding) and Pelletization

Once the dry blends have been produced and have been vacuum conditioned for at least three days, the melt-blending step can begin. A commercially available ZSK-30 twin-screw extruder was fitted with screws designed for melt blending utilizing a vacuum port for purposes of volatilizing residual monomer. The screw design contained several different types of elements, including conveying, compression, mixing and sealing elements. The extruder was fitted with a three-hole die plate, and a chilled water bath with water temperature set between 40 and 70° F. was placed near the extruder outlet. A strand pelletizer and pellet classifier was placed at the end of the water bath. The extruder temperature zones were heated to a temperature of 190 to 210° C., and the vacuum cold traps were set to −20° C. The pre-conditioned dry blend granules were removed from vacuum and placed in a twin-screw feed hopper under nitrogen purge. The extruder screws were set to a speed of 225 RPM, and the feeder was turned on, allowing the dry blend to be fed into the extruder.

The polymer melt blend was allowed to purge through the extruder until the feed was consistent, at which point the vacuum was applied to the vacuum port. The polymer blend extrudate strands were fed through the water bath and into the strand pelletizer. The pelletizer cut the strands into appropriate sized pellets. The pellets were then fed into the classifier and were measured for polymer characteristics such as inherent viscosity, molecular weight and composition. Once the melt-blending process was completed, the pelletized polymer was placed in polyethylene bags, weighed, and stored in a freezer below −20° C. to await devolatilization of residual monomer. Samples of the undried pellets were taken at the start and towards the end of the pelletizing operation were analyzed by gel permeation chromatography revealing considerably lower weight average molecular weights than in the inventive example. GPC and revealed a weight average molecular weight of 38,500 Daltons at the start of the pelletization and 36,800 Daltons towards the end.

Drying of Pellets

The polymer melt-blend was placed into a 3-cubic foot Patterson-Kelley dryer, which was placed under vacuum. The dryer was closed and the pressure was reduced to less than 200 mTorr. Once the pressure was below 200 mTorr, dryer rotation was activated at a rotational speed of 12 RPM with no heat for 6 hours. After the 6 hour period, the oil temperature was set to 110° C. The oil temperature was maintained at 110° C. for a period of 12 hours. At the end of this heating period, the batch was allowed to cool for a period of at least 4 hours, while maintaining rotation and vacuum. The polymer melt-blend pellets were discharged from the dryer by pressurizing the vessel with nitrogen, opening the discharge valve, and allowing the polymer pellets to descend into waiting vessels for long term storage. The storage vessels were air tight and outfitted with valves allowing for evacuation so that the resin was storage under vacuum. The resin was characterized. Gel Permeation chromatography analysis revealed a weight average molecular weight of 40,300 Daltons and a number average molecular weight of 15,200 Daltons. Differential thermal analysis showed a glass transition temperature, $T_g$ of 38° C. and a melting point of 199° C.

Example 9

Dry-Blending, Melt-Blending, Pelletization and Drying of a Comparative Example (Blend of Example 6 and Example 2; 1.7% Acid)

In a manner analogous to Example 7, pellets were prepared starting with a blend of 83 weight percent of the uncapped 90/10 poly(glycolide-co-L(−)-lactide) copolymer of Example 2, and capped 90/10 oligo(glycolide-co-L(−)-lactide) oligomer of Example 6, at 17 weight percent. Melt Blending Molecular Weight Data with times is presented in Table 2.

TABLE 2

Melt Blending Molecular Weight Data

| Sample | $M_w$ ($10^3$ g/mol) | $M_n$ ($10^3$ g/mol) | $M_z$ ($10^3$ g/mol) | $M_w/M_n$ |
|---|---|---|---|---|
| At the Start (14:00) | | | | |
| Injection 1 | 64.6 | 16.8 | 125.1 | 3.85 |
| Injection 2 | 63.6 | 18.4 | 122.5 | 3.45 |
| Injection 3 | 64.0 | 17.1 | 125.5 | 3.75 |
| Average Values | 64.1 | 17.4 | 124.4 | 3.68 |
| In the "Middle" (14:30) | | | | |
| Injection 1 | 62.4 | 18.1 | 119.8 | 3.44 |
| Injection 2 | 63.8 | 17.3 | 124.1 | 3.68 |
| Injection 3 | 62.2 | 17.3 | 122.3 | 3.60 |
| Average Values | 62.8 | 17.6 | 122.1 | 3.57 |
| At the End (15:10) | | | | |
| Injection 1 | 64.7 | 15.8 | 128.3 | 4.09 |
| Injection 2 | 64.2 | 17.3 | 126.0 | 3.72 |
| Injection 3 | 64.0 | 16.7 | 127.1 | 3.83 |
| Average Values | 64.3 | 16.6 | 127.1 | 3.88 |
| After Drying | | | | |
| Injection 1 | 62.7 | 16.3 | 125.0 | 3.86 |
| Injection 2 | 64.8 | 17.2 | 123.3 | 3.78 |
| Average Values | 63.8 | 16.7 | 124.2 | 3.82 |

Example 10

Extrusion and Orientation of the Pellets of Example 7

The polymer melt-blend described in Example 7 was used to produce filaments and, thereafter, bio-absorbable multi-filament braided sutures. Except for the various temperatures the extruder apparatus and the process conditions were substantially the same for all described examples. For example, the spinneret had capillaries of 300 μm in diameter and L/D ratio of 7/1.

The take-up speed for the as-spun filaments was fixed at 1730 feet per minute. The drawing conditions for the examples consisted of a feed roll speed of about 58.8 meters per minute, and a series of other rollers running at speeds corresponding to the following draw ratios: 1.008, 5.000, 1.030, 1.00. This results in an overall (total) draw of 5.191; the collection speed was 305 meters per minute. The roller temperatures for each of the rolls in consecutive order were: 65 to 71° C. (Roller A), 75 to 100° C. (Roller B), 85 to 105° C. (Roller C), and ambient.

Table 3 below, provides the data for the extrusion and orientation conditions for Examples 10, 11 and 12 including die temperatures and orientation roll temperatures.

Table 4 further below, provides the data for the characteristics of the resulting multifilament yarns for this Example 10 and Example 12, including the tenacity, and the elongation-to-break. Small variations in the basic processing conditions resulted in three separate extrudate lots. The oriented yarn mechanical properties results for Example 11 and Example 12 are included in Table 4 as well. The number of filaments for each of these samples was constant at 28.

TABLE 3

Extrusion and Orientation Conditions

| Example No. | Extrudate ID | Die Temperature (° F.) | Oriented Yarn ID | Denier (g/9,000 m) | Roll A (° C.) | Roll B (° C.) | Roll C (° C.) |
|---|---|---|---|---|---|---|---|
| 10 | C1 | 370 | C1-B | 56.3 | 65 | 80 | 85 |
| 10 | 3 | 370 | 3-1 | 55.0 | 70 | 75 | 105 |
| 10 | 6 | 370 | 6-1 | 55.1 | 71 | 75 | 105 |
| 11 | | | Extrudate unsuitable for orientation | | | | |
| 12 | 2 | 405 | 2-2 | 55.3 | 80 | 100 | 105 |
| 12 | 5 | 402 | 5-2 | 55.6 | 80 | 100 | 105 |
| 12 | 6 | 402 | 6-1 | 56.0 | 80 | 100 | 105 |

TABLE 4

Oriented Yarn Mechanical Properties

| Example No. | Extrudate ID | Oriented Yarn ID | Denier (g/9,000 m) | Tenacity (g/d) | Elongation (%) |
|---|---|---|---|---|---|
| 10 | C1 | C1-B | 56.3 | 4.72 | 24.9 |
| 10 | 3 | 3-1 | 55.0 | 4.69 | 25.8 |
| 10 | 6 | 6-1 | 55.1 | 4.47 | 24.4 |
| 12 | 2 | 2-2 | 55.3 | 4.92 | 25.4 |
| 12 | 5 | 5-2 | 55.6 | 4.65 | 24.8 |
| 12 | 6 | 6-1 | 56.0 | 4.98 | 24.2 |

It should be noted that the oriented yarns of Example 10 and Example 12 described in Tables 3-4 exhibit good mechanical properties enabling them to be braided into a variety of useful surgical products including sutures.

Braided sutures of USP size 6/0 to 1 were prepared using the multifilament yarns resulting from the yarn of Example 10 and Example 12. These sutures showed an average high initial straight tensile strength and high knot strength. Furthermore, they exhibited an in vivo breaking strength retention profiles in which all or at least most of the tensile strength was lost at 14 days. This characteristic is consistent with a "fast absorbing suture." The sutures made using the process of the present invention had excellent handling characteristics and were essentially entirely absorbed in vivo within about 42 days; again consistent with a "fast absorbing suture."

Example 11

Attempted Extrusion of the Resin of Example 8

In a manner similar to Example 10, attempts were made to extrude the polymer melt-blend described in Example 8 to produce filaments with suitable mechanical properties. Although a broad variety of conditions were investigated, all attempts failed, most likely due to the low molecular weight nature of this particular resin (a weight average molecular weight of 38,000 Daltons).

Example 12

Extrusion and Orientation of the Resin of Example 9

In a manner similar to Example 10, the polymer melt-blend described in Example 9 was used to produce filaments and, thereafter, bio-absorbable multifilament braided sutures.

The data for the characteristics of the resulting multifilament yarns for this Example 12 can be found in Table 4 above.

The yarns of this Example 12 exhibit good mechanical properties enabling them to be braided into a variety of useful surgical products including sutures.

Example 13

Braiding, Scouring, Hot Stretching and Annealing of Oriented Yarn

The yarns from Example 10 and Example 12 were braided, scoured in ethyl acetate, hot stretched and annealed in a conventional manner. The resulting annealed braid will be referred to as the annealed braid of Example 13.

Example 14

Coating and Pliabilization of the Annealed Braids

The annealed braid of Example 13 was coated and pliabilized in a conventional manner.

Example 15

Needle Attachment, Packaging and Sterilization

The coated braid of Example 14 was packaged and ethylene oxide sterilized in a conventional manner.

Example 16

Analytical Results

In general, the resins and fibers of the present invention were characterized for chemical composition by Nuclear Magnetic Resonance (NMR); for molecular weight by inherent viscosity in hexafluoroisopropanol at 0.1 g/dL at 25° C., and/or gel permeation chromatography (GPC); and for morphology by X-ray diffraction, and differential scanning calorimetry (DSC). Analysis was performed on fibers prior to annealing, after annealing, and often after EO sterilization.

Example 17

Mechanical Properties and In Vitro Testing

The size 2/0 EO sterilized coated braids of Example 15 were tested for mechanical properties and underwent in vitro testing. The processes employed will now be described. The selected lot was tested for mechanical properties using an INSTRON tensile testing machine, Model 5544 fitted with an appropriate load cell. The articles were placed in a fixture designed to appropriately grip and the force-to-break was recorded as "Zero-Day Breaking Strength".

Samples of the EO sterilized coated braids of Example 15 were placed in containers filled with a suitable amount of phosphate buffer at pH 7.27. The containers were then incubated at 37° C. and a representative sample size, typically eight, was retrieved periodically for mechanical testing. The incubated articles were tested for their mechanical properties using an INSTRON tensile testing machine in a fashion similar to the above mentioned method. The force-to-break was recorded as "Breaking Strength". The ratio of "Breaking Strength" to "Zero-Day Breaking Strength" was calculated and reported as "Breaking Strength Retention" for each time period.

The in vitro testing results of the size 2/0 EO sterilized coated braids of Example 15 are shown directly below in Table 5.

TABLE 5

| Braids of Example 15, Test Number | Incubation Time in pH 7.27 Buffer at 37° C. | | | | | |
|---|---|---|---|---|---|---|
| | 0 Day | 5 Day | 7 Day | 10 Day | 14 Day | 17 Day |
| 1 | 11.72 | 7.76 | 6.07 | 2.32 | 0.24 | 0.06 |
| 2 | 11.33 | 7.85 | 6.09 | 2.36 | 0.28 | 0.10 |
| 3 | 10.81 | 8.06 | 5.67 | 2.28 | 0.10 | 0.12 |
| 4 | 11.11 | 7.92 | 6.14 | 2.18 | 0.32 | 0.09 |
| 5 | 11.31 | 7.52 | 6.11 | 1.60 | 0.21 | 0.09 |
| 6 | 11.33 | 8.30 | 5.63 | 2.02 | 0.14 | 0.05 |

TABLE 5-continued

| Braids of Example 15, Test | Incubation Time in pH 7.27 Buffer at 37° C. | | | | | |
|---|---|---|---|---|---|---|
| Number | 0 Day | 5 Day | 7 Day | 10 Day | 14 Day | 17 Day |
| 7 | 10.77 | 7.65 | 6.53 | 1.86 | 0.27 | 0.10 |
| 8 | 11.00 | 8.20 | 6.12 | 1.97 | 0.12 | 0.13 |
| Average | 11.17 | 7.91 | 6.05 | 2.07 | 0.21 | 0.09 |
| S.D. | 0.32 | 0.27 | 0.29 | 0.26 | 0.08 | 0.03 |

The in vitro testing results of the size 2/0 EO sterilized coated braids of Example 15, expressed as percent strength remaining, are shown directly below in Table 6.

TABLE 6

| | Percent Strength Remaining After Incubation in pH 7.27 Buffer at 37° C. for the Indicated Times | | | | | |
|---|---|---|---|---|---|---|
| | 0 Day | 5 Day | 7 Day | 10 Day | 14 Day | 17 Day |
| Braids of Example 15 | 100 | 71 | 54 | 19 | 1.9 | 0.8 |

Example 18

In Vivo Breaking Strength Retention Testing

The size 2/0, EO sterilized, coated braids of Example 15, underwent in vivo testing to assess breaking strength retention post-implantation. The testing was conducted in a conventional manner. The testing results are shown directly below in Table 7.

TABLE 7

| Braids of Example 15, Test | Strength (in lbs) of Size 2/0 Sutures at the Indicated Time Post-Implantation | | | | | |
|---|---|---|---|---|---|---|
| Number | 0 Day | 5 Day | 7 Day | 10 Day | 14 Day | 17 Day |
| 1 | 10.54 | 7.44 | 6.22 | 3.02 | 0.10 | — |
| 2 | 10.86 | 7.41 | 6.01 | 2.28 | 0.14 | — |
| 3 | 10.79 | 7.65 | 6.10 | 2.90 | 0.18 | — |
| 4 | 10.33 | 7.37 | 6.14 | 2.91 | 0.27 | — |
| 5 | 10.06 | 7.72 | 6.59 | 3.16 | 0.25 | — |
| 6 | 10.86 | 7.79 | 6.32 | 2.80 | 0.12 | — |
| 7 | 11.10 | 7.46 | 6.04 | 2.57 | 0.15 | — |
| 8 | 10.56 | 7.73 | 5.87 | 3.07 | 0.11 | — |
| Average | 10.64 | 7.57 | 6.16 | 2.84 | 0.17 | 0.00 |
| S.D. | 0.33 | 0.17 | 0.22 | 0.29 | 0.06 | 0.00 |

The in vivo testing results of the size 2/0 EO sterilized coated braids of Example 15, expressed as percent strength remaining, are shown directly below in Table 8.

TABLE 8

| | Percent Strength Remaining Post-Implantation for the Indicated Times | | | | | |
|---|---|---|---|---|---|---|
| | 0 Day | 5 Day | 7 Day | 10 Day | 14 Day | 17 Day |
| Braids of Example 15 | 100 | 71 | 58 | 27 | 1.6 | 0.0 |

Agreement between the in vitro testing results and the in vivo testing results was good, as shown in the Table 9 below:

TABLE 9

| Braids of | Percent Strength Remaining | | | | | |
|---|---|---|---|---|---|---|
| Example 15 | 0 Day | 5 Day | 7 Day | 10 Day | 14 Day | 17 Day |
| In Vitro | 100 | 71 | 54 | 19 | 1.9 | 0.8 |
| In Vivo | 100 | 71 | 58 | 27 | 1.6 | 0.0 |

Example 19

In Vivo Total Absorption

The coated braids of Example 14 underwent in vivo testing to assess absorption and tissue reaction characteristics. The testing was conducted in a conventional manner.

Example 20

Information for MW Data on Various Braids

Additional data for the inventive blends and devices made of the inventive blends is shown in Tables 10-12.

TABLE 10

| | Processing Data of EO-Sterilized Size 2/0 Triclosan-Coated Sutures | | | |
|---|---|---|---|---|
| Polymer | Blend IV | Die Temp [° F.] | Yarn tenacity [gpd] | Coated Lot # |
| P20-1 | 1.23 | 421 | 6.60 | C20-1 |
| P20-1 | 1.23 | 411 | 5.10 | C20-2 |
| P20-2 | 1.18 | 411 | 5.40 | C20-3 |
| P20-2 | 1.18 | 431 | 5.90 | C20-4 |
| P12-3 | 1.24 | 421 | 6.10 | C20-5 |
| P20-3 | 1.24 | 431 | 6.20 | C20-6 |
| P20-4 | 1.32 | 441 | 5.90 | C20-7 |
| P20-4 | 1.32 | 451 | 5.20 | C20-8 |
| P20-3 | 1.24 | 441 | 4.90 | C20-9 |

TABLE 11

| | Molecular Weight Testing of Non-Sterile Braid | | | | |
|---|---|---|---|---|---|
| Sample Description | $M_w$ ($10^3$ g/mol) | $M_n$ ($10^3$ g/mol) | $M_z$ ($10^3$ g/mol) | $M_w/M_n$ | IV (dL/g) |
| C20-1 | 43.3 | 15.6 | 76.6 | 2.79 | 0.99 |
| C20-2 | 43.1 | 15.8 | 76.7 | 2.73 | 0.98 |
| C20-3 | 40.6 | 15.7 | 70.9 | 2.60 | 0.97 |
| C20-4 | 41.1 | 16.2 | 71.0 | 2.54 | 0.94 |
| C20-5 | 46.4 | 17.9 | 79.1 | 2.60 | 0.98 |
| C20-6 | 44.5 | 15.9 | 79.1 | 2.80 | 0.99 |
| C20-7 | 46.2 | 16.7 | 81.4 | 2.78 | 1.01 |
| C20-8 | 43.3 | 17.1 | 74.7 | 2.54 | 0.97 |
| C20-9 | 45.9 | 17.8 | 79.5 | 2.60 | 0.99 |

TABLE 12

| | Molecular Weight Testing of EO-Sterilized Braid | | | | |
|---|---|---|---|---|---|
| Sample Description | $M_w$ ($10^3$ g/mol) | $M_n$ ($10^3$ g/mol) | $M_z$ ($10^3$ g/mol) | $M_w/M_n$ | IV (dL/g) |
| C20-1S | 43.4 | 16.5 | 75.9 | 2.65 | 0.95 |
| C20-2S | 43.3 | 16.0 | 76.2 | 2.71 | 0.96 |
| C20-3S | 41.4 | 15.6 | 72.9 | 2.66 | 0.93 |
| C20-4S | 39.6 | 15.0 | 71.1 | 2.65 | 0.92 |

TABLE 12-continued

Molecular Weight Testing of EO-Sterilized Braid

| Sample Description | $M_w$ ($10^3$ g/mol) | $M_n$ ($10^3$ g/mol) | $M_z$ ($10^3$ g/mol) | $M_w/M_n$ | IV (dL/g) |
|---|---|---|---|---|---|
| C20-5S | 46.4 | 18.0 | 79.6 | 2.58 | 0.97 |
| C20-6S | 45.2 | 17.3 | 78.9 | 2.61 | 0.96 |
| C20-7S | 46.1 | 17.3 | 81.0 | 2.67 | 0.97 |
| C20-8S | 46.0 | 20.7 | 84.9 | 2.23 | 0.94 |
| C20-9S | 44.8 | 17.1 | 78.5 | 2.62 | 0.96 |

Example 21

Strength and In Vitro Performance Comparisons

Polymeric blends of the subject invention based on 10/90 poly(L(−)-lactide-co-glycolide) were made into braided sutures of various sizes to compare against commercial sutures prepared from the same base resin, 10/90 poly(L(−)-lactide-co-glycolide). These commercial sutures had been treated to achieve an accelerated absorption profile: essentially no strength remaining at 14 days post-implantation and essentially absorbed at 42 days post-implantation. Breaking strength values obtained at various times of incubation in vitro under the testing conditions of 37° C. and pH 7.27 were obtained. Comparison of the initial breaking strength and strength after five days of in vitro incubation at 37° C. and pH 7.27 of variously sized sutures of the present invention and of similar sutures consisting essentially of the first polymeric component are shown in Table 13. The latter are commercial 10/90 poly(L(−)-lactide-co-glycolide) sutures that had been treated as part of the manufacturing process to achieve an accelerated absorption profile of essentially no strength remaining at 14 days post-implantation and essentially absorbed at 42 days post-implantation.

TABLE 13

Comparison of the Breaking Strength of Variously Sized Sutures of the Present Invention and of Similar Sutures Consisting Essentially of the First Polymeric Component; Initial Strength and Strength after Five Days of In Vitro Incubation at 37° C. and pH 7.27

| | Suture of the Present Invention | | Similar Suture Consisting Essentially of the First Polymeric Component | |
|---|---|---|---|---|
| USP Suture Size | Initial Strength [lbs] | Strength at 5 Days Incubation [lbs] | Initial Strength [lbs] | Strength at 5 Days Incubation [lbs] |
| Size 1 | 23.70 | 17.02 | 18.23 | 9.26 |
| Size 0 | 18.60 | 12.84 | 13.33 | 6.92 |
| Size 2/0 | 13.80 | 9.85 | 9.71 | 4.90 |
| Size 3/0 | 8.64 | 6.66 | 6.36 | 3.45 |
| Size 4/0 | 5.90 | 4.20 | 4.13 | 2.27 |
| Size 5/0 | 3.41 | 2.33 | 2.36 | 1.15 |
| Size 6/0 | 1.32 | 0.90 | 1.10 | 0.62 |
| Size 7/0 | | | | 0.35 |
| Size 8/0 | | | | 0.26 |

Diameter measurements on the sutures shown above were approximately 19, 16, 13, 10, 8, 6, 3.3 2.4 and 1.8 mils for the sutures sizes 1, 0, 2/0, 3/0, 4/0, 5/0, 6/0, 7/0 and 8/0, respectively.

The novel bioabsorbable polymeric compositions and blends of the present invention have many advantages including providing medical devices that have improved mechanical properties with precisely controllable absorption rates. The advantages of the novel polymer blends of the present invention are also apparent from the graphs of data in FIGS. 4-7.

Although this invention has been shown and described with respect to detailed embodiments thereof, it will be understood by those skilled in the art that various changes in form and detail thereof may be made without departing from the spirit and scope of the claimed invention. It will be understood that the embodiments described herein are merely exemplary and that a person skilled in the art may make many variations and modifications, including but not limited to those discussed hereinabove, without departing from the spirit and scope of the present invention. All such variations and modifications are intended to be included within the scope of the invention as defined in the appended claims.

We claim:

1. A suture, comprising an absorbable polymer blend, the blend comprising:
a mixture of a polymer and an oligomer, wherein the polymer has a weight average molecular weight higher than the weight average molecular weight of the oligomer, and wherein the weight average molecular weight of the oligomer is about 1,400 Daltons to about 5,200 Daltons,
wherein at least about 100% of the absorbable oligomer is end-capped on both ends by carboxylic acid groups and about 0% of the polymer is end-capped by carboxylic acid groups, and wherein a suture made from said blend and having a size has a pre-implantation strength equivalent to or greater than the pre-implantation strength of a similar suture one size larger, said similar suture consisting essentially of the first component, wherein said suture and said similar suture have a substantially equivalent time to achieve zero mechanical strength.

2. The suture of claim 1, wherein the polymer blend has an inherent viscosity of about 0.5 dL/g to about 1.8 dL/g.

3. The suture of claim 1, wherein the weight average molecular weight of the polymer blend is about 18,000 Daltons to about 100,000 Daltons.

4. The suture of claim 1, said device coated with a medically useful substance.

5. The suture of claim 1, wherein at least a part of the suture comprises a plurality of yarns or filaments.

6. The suture of claim 1, wherein the suture is a monofilament.

7. The suture of claim 1, wherein said suture comprises a plurality of filaments, the filaments a blend of poly(lactide-co-glycolide) copolymer comprising about 88 wt. % to about 92 wt. % of polymerized glycolide and about 8 wt. % to about 12 wt. % of polymerized lactide, wherein the suture has a diameter of about 19 mils,
a minimum pre-implantation tensile strength of about 20 pounds,
a minimum tensile strength of about 12 pounds at 5 days post-implantation, substantially no tensile strength at 14 days post-implantation,
and wherein the suture is substantially absorbed in about 42 days post-implantation.

8. The suture of claim 1, wherein said suture comprises a plurality of filaments, the filaments comprising a blend of poly(lactide-co-glycolide) copolymer, said copolymer comprising about 88 wt. % to about 92 wt. % of polymerized glycolide and about 8 wt. % to about 12 wt. % of polymerized lactide, wherein the suture has a diameter of about 16 mils, a minimum pre-implantation tensile strength of about 15 pounds, a minimum tensile strength of about 9.5 pounds at 5 days post-implantation, from substantially no tensile strength to about 5% of the pre-implantation tensile strength at 14 days post-implantation, and, wherein the suture is substantially absorbed in about 42 days post-implantation.

9. The suture of claim 1, wherein said suture comprises a plurality of filaments, the filaments comprising a blend of poly(lactide-co-glycolide) copolymer, said copolymer comprising about 88 wt. % to about 92 wt. % of polymerized glycolide and about 8 wt. % to about 12 wt. % of polymerized lactide,
wherein the suture has a diameter of about 13 mils, a minimum pre-implantation tensile strength of about 11 pounds, a minimum tensile strength of about 7 pounds at 5 days post-implantation, substantially no tensile strength at 14 days post-implantation, and, wherein the suture is substantially absorbed in about 42 days post-implantation.

10. The suture of claim 1, wherein said suture comprises a plurality of filaments, the filaments comprising a blend of poly(lactide-co-glycolide) copolymer, said copolymer comprising about 88 wt. % to about 92 wt. % of polymerized glycolide and about 8 wt. % to about wt. % 12 of polymerized lactide,
wherein the suture has a diameter of about 10 mils, a minimum pre-implantation tensile strength of about 7.5 pounds, a minimum tensile strength of about 4.5 pounds at 5 days post-implantation, substantially no tensile strength at 14 days post-implantation, and, wherein the suture is substantially absorbed in about 42 days post-implantation.

11. The suture of claim 1, wherein said suture comprises a plurality of filaments, the filaments comprising a blend of poly(lactide-co-glycolide) copolymer, said copolymer comprising about 88 wt. % to about 92 wt. % of polymerized glycolide and about 8 wt. % to about 12 wt. % of polymerized lactide,
wherein the suture has a diameter of about 8 mils, a minimum pre-implantation tensile strength of about 4.6 pounds, a minimum tensile strength of about 3 pounds at 5 days post-implantation, substantially no tensile strength at 14 days post-implantation, and, wherein the suture is substantially absorbed in about 42 days post-implantation.

12. The suture of claim 1, wherein said suture comprises a plurality of filaments, the filaments comprising a blend of poly(lactide-co-glycolide) copolymer, said copolymer comprising about 88 wt. % to about 92 wt. % of polymerized glycolide and about 8 wt. % to about 12 wt. % of polymerized lactide,
wherein the suture has a diameter of about 6 mils, a minimum pre-implantation tensile strength of about 2.6 pounds, a minimum tensile strength of about 1.6 pounds at 5 days post-implantation, substantially no tensile strength at 14 days post-implantation, and, wherein the suture is substantially absorbed in about 42 days post-implantation.

13. The suture of claim 1, wherein said suture comprises a plurality of filaments, the filaments comprising a blend of poly(lactide-co-glycolide) copolymer, said copolymer comprising about 88 wt. % to about 92 wt. % of polymerized glycolide and about 8 wt. % to about 12 wt. % of polymerized lactide,
wherein the suture has a diameter of about 3.3 mils, a minimum pre-implantation tensile strength of about 1.2 pound, a minimum tensile strength of about 0.75 pounds at 5 days post-implantation, substantially no tensile strength at 14 days post-implantation, and, wherein the suture is substantially absorbed in about 42 days post-implantation.

14. The suture of claim 1, wherein said suture comprises a plurality of filaments, the filaments comprising a blend of poly(lactide-co-glycolide) copolymer, said copolymer comprising about 88 wt. % to about 92 wt. % of polymerized glycolide and about 8 wt. % to about 12 wt. % of polymerized lactide,
wherein the suture has a diameter of about 2.4 mils, a minimum pre-implantation tensile strength of about 0.53 pounds, a minimum tensile strength of about 0.40 pounds at 5 days post-implantation, substantially no tensile strength at 14 days post-implantation, and, wherein the suture is substantially absorbed in about 42 days post-implantation.

15. The suture of claim 1, wherein said suture comprises a plurality of filaments, the filaments comprising a blend of poly(lactide-co-glycolide) copolymer, the copolymer comprising about 88 wt. % to about 92 wt. % of polymerized glycolide and about 8 wt. % to about 12 wt. % of polymerized lactide,
wherein the suture has a diameter of about 1.8 mils, a minimum pre-implantation tensile strength of about 0.45 pounds, a minimum tensile strength of about 0.30 pounds at 5 days post-implantation, substantially no tensile strength at 14 days post-implantation, and, wherein the suture is substantially absorbed in about 42 days post-implantation.

* * * * *